United States Patent [19]
Franckowiak et al.

[11] Patent Number: 4,753,936
[45] Date of Patent: Jun. 28, 1988

[54] CIRCULATION-ACTIVE SUBSTITUTED 1,4-DIHYDROPYRIDINE-3-CARBOXYLIC ACID PIPERAZIDES

[75] Inventors: Gerhard Franckowiak, Wuppertal, Fed. Rep. of Germany; Günther Thomas, Garbagnate/Milano, Italy; Matthias Schramm, Koeln; Michael Kayser, Hagen; Rainer Gross; Martin Bechem, both of Wuppertal, all of Fed. Rep. of Germany

[73] Assignee: Bayer Aktiengesellschaft, Leverkusen, Fed. Rep. of Germany

[21] Appl. No.: 2,094

[22] Filed: Jan. 12, 1987

[30] Foreign Application Priority Data

Jan. 18, 1986 [DE] Fed. Rep. of Germany ....... 3601397

[51] Int. Cl.$^4$ ................ A61K 31/495; C07D 401/06; C07D 401/14; C07D 413/14
[52] U.S. Cl. ............................ 514/227.8; 514/252; 544/121; 544/295; 544/357; 544/364; 544/365; 514/228.2; 514/228.5; 514/234.2; 514/233.5; 514/235.2; 514/235.8
[58] Field of Search .............. 544/121, 295, 357, 364, 544/365; 514/236, 252

[56] References Cited

U.S. PATENT DOCUMENTS 4,031,104 6/1977 Bossert et al. .................. 546/321
4,656,181 4/1987 Sunkel et al. .................. 514/336

FOREIGN PATENT DOCUMENTS 0083315 7/1983 European Pat. Off. .
0097821 1/1984 European Pat. Off. .
0111453 6/1984 European Pat. Off. .
0123112 10/1984 European Pat. Off. .
174653 3/1986 European Pat. Off. ............ 544/365
2228377 1/1974 Fed. Rep. of Germany .
3445356 6/1985 Fed. Rep. of Germany .
48970 3/1985 Japan ................................. 544/365

Primary Examiner—Richard A. Schwartz
Assistant Examiner—Dale A. Bjorkman
Attorney, Agent, or Firm—Sprung Horn Kramer & Woods

[57] ABSTRACT

1,4-Dihydropyridine-3-carboxylic acid piperazides of the formula

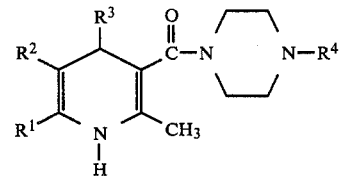

in which
$R^1$ is CN or alkyl, preferably methyl,
$R^2$ is H, CN, $NO_2$ or preferably carboxyalkyl,
$R^3$ is aryl or heterocyclic, and
$R^4$ is alkyl, cycloalkyl, aryl or an acyl radical, and physiologically acceptable salts thereof, are circulation active. Novel intermediates are also provided.

10 Claims, No Drawings

CIRCULATION-ACTIVE SUBSTITUTED 1,4-DIHYDROPYRIDINE-3-CARBOXYLIC ACID PIPERAZIDES

The invention relates to 1,4-dihydropyridine-3-carboxylic acid piperazides, to process for their preparation and to their use in medicaments.

It is known that 1,4-dihydropyridines have vasodilating properties and can be used as antihypertensives (compare DE-OS (German Published Specification) No. 2,629,892 and DE-OS (German Published Specification) No. 2,752,820).

It is also known that dihydropyridinecarboxamides effect limitation of the contractility of the smooth and cardiac muscles and can be used for the treatment of coronary and vascular diseases (compare DE-OS (German Published Specification) No. 2,228,377).

The invention relates to 1,4-dihydropyridine-3-carboxylic acid piperazides of the general formula I

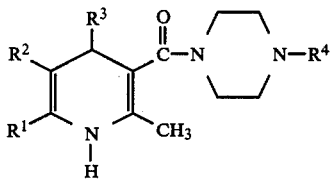

in which
$R^1$ represents cyano or represents straight-chain or branched $C_1$–$C_6$-alkyl which is optionally substituted by halogen, hydroxyl or $C_2$–$C_7$-acyloxy,
$R^2$ represents hydrogen, represents cyano, represents nitro or represents the group $CO_2R^5$, $R^5$ denoting straight-chain or branched $C_1$–$C_8$-alkyl which is optionally substituted by hydroxyl, halogen, cyano, $C_1$–$C_8$-alkoxy, $C_1$–$C_8$-alkylthio, phenyl, amino, $C_1$–$C_6$-alkylamino, di-$C_1$–$C_6$-alkylamino, phenylamino, $C_2$–$C_7$-acylamino or $C_1$–$C_6$-alkyl-benzylamino,
$R^3$ represents $C_6$–$C_{12}$-aryl which is optionally substituted once or several times, identically or differently, by halogen, nitro, cyano, $C_1$–$C_8$-alkyl, $C_1$–$C_8$-alkoxy, $C_1$–$C_8$-alkylthio, $C_7$–$C_{14}$-aralkyl, $C_7$–$C_{14}$-aralkoxy or $C_7$–$C_{14}$-aralkylthio, it being possible for each of the aryl radicals in turn to be substituted by nitro, trifluoromethyl, cyano, methoxy, methylthio, trifluoromethoxy, difluoromethoxy, halogen or $C_1$–$C_6$-alkyl, or is optionally substituted by trifluoromethyl, trifluoromethylthio, trifluoromethoxy, difluoromethoxy, amino, $C_1$–$C_6$-alkylamino, di-$C_1$–$C_6$-alkylamino or by $C_2$–$C_7$-acylamino, or represents a heterocycle from the series comprising pyridyl, thienyl, furyl, pyrrolyl, quinolyl, isoquinolyl, pyrimidyl, benzoxadiazolyl, imidazolyl, thiazolyl, oxazolyl, chromenyl, or thiochromenyl, the heterocycle optionally being substituted by phenyl, $C_1$–$C_6$-alkyl, $C_1$–$C_6$-alkoxy, $C_1$–$C_6$-alkylthio, trifluoromethyl, trifluoromethoxy, trifluoromethylthio, halogen, amino, $C_1$–$C_6$-alkylamino, di-$C_1$–$C_6$-alkylamino or $C_2$–$C_7$-acylamino, and
$R^4$ represents $C_6$–$C_{12}$-aryl which is optionally substituted once or several times, identically or differently, by halogen, nitro, cyano, $C_1$–$C_8$-alkyl, $C_1$–$C_8$-alkoxy, $C_1$–$C_8$-alkylthio, trifluoromethyl, trifluoromethoxy, trifluoromethylthio, difluoromethoxy, hydroxyl, amino, $C_1$–$C_6$-alkylamino, di-$C_1$–$C_6$-alkylamino or $C_2$–$C_7$-acylamino, or represents straight-chain, branched or cyclic $C_1$–$C_{20}$-alkyl, $C_2$–$C_{20}$-alkenyl or $C_2$–$C_{20}$-alkynyl, each of which can optionally be substituted by halogen, $C_1$–$C_8$-alkoxy, $C_1$–$C_8$-alkylthio, amino, $C_1$–$C_8$-alkylamino, di-$C_1$–$C_8$-alkylamino, $C_2$–$C_7$-acylamino, piperidino, piperazino, morpholino, thiomorpholino, pyrrolidino or by $C_6$–$C_{12}$-aryl, it being possible for aryl in turn to carry one or more substituents from the group comprising nitro, cyano, trifluoromethyl, halogen, $C_1$–$C_8$-alkyl, $C_1$–$C_8$-alkylthio or $C_1$–$C_8$-alkoxy, or is substituted by the group $COR^6$,
$R^6$ representing hydrogen, representing hydroxyl, representing $C_1$–$C_8$-alkoxy or representing the group

$R^7$ and $R^8$ being identical or different and denoting hydrogen, $C_1$–$C_8$-alkyl, $C_6$–$C_{12}$-aryl, $C_7$–$C_{14}$-aralkyl or $C_2$–$C_7$-acyl, or
$R^7$ and $R^8$ together forming a 5–7-membered saturated or unsaturated ring which can contain as further hetero atoms nitrogen, sulphur and/or oxygen, or
$R^4$ represents the group $COR^6$,
$R^6$ having the abovementioned meaning,
in the form of their isomers, isomer mixtures, racemates and optical antipodes, and to their physiologically acceptable salts.

Preferred compounds of the general formula I are those
in which
$R^1$ represents straight-chain or branched $C_1$–$C_4$-alkyl, which is optionally substituted by one or more fluorine, chlorine, bromine, hydroxyl, benzoyloxy or acetyloxy,
$R^2$ represents cyano, represents nitro, or represents the group $CO_2R^5$,
$R^5$ denoting straight-chain or branched $C_1$–$C_6$-alkyl which is optionally substituted by one or more fluorine, chlorine, bromine, cyano, phenyl, $C_1$–$C_6$-alkoxy, $C_1$–$C_6$-alkylthio, amino, $C_1$–$C_4$-alkylamino, di-$C_1$–$C_4$-alkylamino, acetylamino or benzylmethylamino,
$R^3$ represents phenyl which is optionally substituted up to four times, identically or differently, by fluorine, chlorine, bromine, nitro, cyano, $C_1$–$C_6$-alkyl, $C_1$–$C_6$-alkoxy, $C_1$–$C_6$-alkylthio, benzyl, benzyloxy or benzylthio, it being possible for each of the phenyl radicals in turn to be substituted by nitro, trifluoromethyl, trifluoromethoxy, trifluoromethylthio, methoxy, fluorine, chlorine, bromine or $C_1$–$C_4$-alkyl, or is substituted by trifluoromethyl, trifluoromethoxy, difluoromethoxy, amino, $C_1$–$C_4$-alkylamino, di-$C_1$–$C_4$-alkylamino or acetylamino or acetylamino, or represents pyridyl, thienyl, furyl, pyrimidyl, benzoxadiazolyl, 2-phenyl-thiochromen-8-yl or quinolyl, and
$R^4$ represents phenyl which is optionally substituted up to four times, identically or differently, by fluorine, chlorine, bromine, nitro, cyano, $C_1$–$C_6$-alkyl, $C_1$–$C_6$-alkoxy, $C_1$–$C_6$-alkylthio, trifluoromethyl, difluoromethoxy, hydroxyl, amino, $C_1$–$C_3$-alkylamino, di-$C_1$–$C_3$-alkylamino or acetylamino, or represents straight-chain, branched or cyclic $C_1$–$C_{15}$-alkyl, $C_2$–$C_{15}$-alkenyl or $C_2$–$C_{15}$-alkynyl, each of which is optionally substituted by fluorine, chlorine, bromine, $C_1$-$C_6$-alkoxy, $C_1$-$C_6$-alkylthio, amino, $C_1$-$C_6$-alkylamino, di-$C_1$-$C_6$-alkylamino, acetylamino, benzoylamino or by phenyl, it being possible for the phenyl radical in turn to carry one to three substituents from the group comprising nitro, trifluoromethyl, fluorine, chlorine, bromine, $C_1$-$C_6$-alkyl, $C_1$-$C_6$-alkoxy or $C_1$-$C_6$-alkylthio, or is substituted by the group $COR^6$, $R^6$ representing hydrogen, representing hydroxyl, representing $C_1$-$C_6$-alkoxy or representing the group

$R^7$ and $R^8$ being identical or different and representing hydrogen, representing $C_1$-$C_6$-alkyl, representing phenyl, representing benzyl, representing acetyl or representing benzoyl, or $R^7$ and $R^8$ together with the nitrogen atom forming a heterocycle from the series comprising pyrrolidine, piperidine, morpholine, thiomorpholine, imidazolidine, piperazine or pyrroline, or $R^4$ represents the group of the formula $COR^6$, $R^6$ having the abovementioned meaning, in the form of their isomers, isomer mixtures, racemates or optical antipodes, and their physiologically acceptable salts.

Particularly preferred compounds of the formula I are those
in which $R^1$ represents methyl or ethyl, each of which is optionally substituted by chlorine, bromine or acetyloxy, $R^2$ represents cyano, represents nitro or represents the group $CO_2R^5$, $R^5$ denoting straight-chain or branched $C_1$-$C_4$-alkyl which is optionally substituted by one or more fluorine, cyano, $C_1$-$C_4$-alkoxy, $C_1$-$C_4$-alkylthio or N-benzylmethylamino, $R^3$ represents phenyl which is optionally substituted up to three times, identically or differently, by fluorine, chlorine, nitro, cyano, $C_1$-$C_4$-alkyl, $C_1$-$C_4$-alkoxy, $C_1$-$C_4$-alkylthio, benzyl, benzyloxy or benzylthio, it being possible for the phenyl radicals in turn to be substituted up to twice by nitro, trifluoromethyl, methoxy, fluorine, chlorine, methyl or ethyl, or is substituted by trifluoromethyl or trifluoromethoxy, or represents pyridyl, thienyl, furyl, pyrimidyl or benzoxadiazolyl or 2-phenyl-thiochromen-8-yl, and $R^4$ represents phenyl which is optionally substituted up to twice, identically or differently, by fluorine, chlorine, nitro, $C_1$-$C_4$ alkyl, $C_1$-$C_4$-alkoxy, $C_1$-$C_4$-alkylthio or trifluoromethoxy, or represents straight-chain, branched or cyclic $C_1$-$C_{10}$-alkyl, $C_2$-$C_{10}$-alkenyl or $C_2$-$C_{10}$-alkynyl, each of which is optionally substituted by fluorine, chlorine, $C_1$-$C_4$-alkoxy, $C_1$-$C_4$-alkylthio, amino, $C_1$-$C_4$-alkylamino, di-$C_1$-$C_4$-alkylamino, acetylamino or by phenyl, it being possible for phenyl in turn to carry one to two substituents from the group comprising nitro, trifluoromethyl, fluorine, chlorine, $C_1$-$C_4$-alkoxy or $C_1$-$C_4$-alkyl, or is substituted by the group $COR^6$, $R^6$ representing hydrogen, representing hydroxyl, representing $C_1$-$C_4$-alkoxy or representing the group

$R^7$ and $R^8$ being identical or different and representing hydrogen, representing $C_1$-$C_4$-alkyl, representing phenyl, representing benzyl or representing acetyl, or $R^7$ and $R^8$, together with the nitrogen atom, form a heterocycle from the series comprising pyrrolidine, piperidine, morpholine or thiomorpholine, or $R^4$ represents the group $COR^6$, $R^6$ having the abovementioned meaning, in the form of their isomers, isomer mixtures, racemates or optical antipodes, and their physiologically acceptable salts.

Physiologically acceptable salts of the substances according to the invention can be salts with inorganic or organic acids. Examples which may be mentioned are: hydrohalides, such as hydrobromides, hydrochlorides, hydrogen sulphates, sulphates, hydrogen phosphates, acetates, maleates, fumarates, citrates, tartrates, lactates or benzoates.

The compounds according to the invention, of the general formula I in which $R^1$-$R^4$ have the abovementioned meaning, are obtained when

[A] aldehydes of the general formula (II)

in which $R^3$ has the abovementioned meaning, and keto compounds of the general formula (III)

in which $R^2$ and $R^3$ have the abovementioned meaning, are reacted with keto compounds of the general formula (IV)

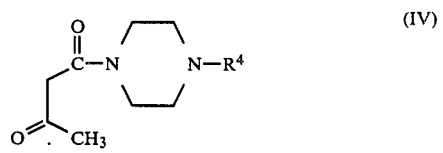

in which $R^4$ has the abovementioned meaning, and ammonia, where appropriate in the presence of water or inert organic solvents, or when

[B] aldehydes of the general formula (II) are reacted with keto compounds of the general formula (III) and enamines of the general formula (V)

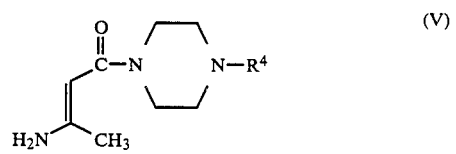

in which $R^4$ has the abovementioned meaning, where appropriate in the presence of water or inert organic solvents, or when

[C] aldehydes of the general formula (II) are reacted with keto compounds of the general formula (IV) and enamines of the general formula (VI)

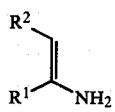
(VI)

in which $R^1$ and $R^2$ have the abovementioned meaning, where appropriate in the presence of water or inert organic solvents, or when

[D] keto compounds of the general formula (III) and ammonia are reacted with ylidene compounds of the general formula (VII)

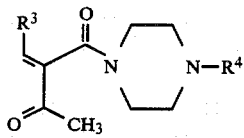
(VII)

in which $R^3$ and $R^4$ have the abovementioned meaning, where appropriate in the presence of water or inert organic solvents, or when

[E] keto compounds of the general formula (IV) and ammonia are reacted with ylidene compounds of the general formula (VIII)

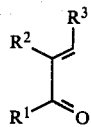
(VIII)

in which $R^1$–$R_3$ have the abovementioned meaning, where appropriate in the presence of water or inert organic solvents, or when

[F] enamines of the general formula (VI) are reacted with ylidene compounds of the general formula (VII), where appropriate in the presence of water or inert organic solvents, or when

[G] enamines of the general formula (V) are reacted with ylidene compounds of the general formula (VIII), where appropriate in the presence of water or inert organic solvents, or when

[H] 1,4-dihydropyridinecarboxylic acids of the general formula (IX)

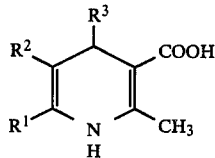
(IX)

in which $R^1$–$R^3$ have the abovementioned meaning, are reacted by known methods, where appropriate via a reactive acid derivative, with compounds of the general formula (X)

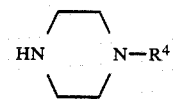
(X)

in which $R^4$ has the abovementioned meaning, where appropriate in the presence of an inert organic solvent.

Examples of reactive acid derivatives which may be mentioned are: activated esters, hydroxysuccinimide esters, acid imidazolides, acid halides, mixed anhydrides, reaction with cyclohexylcarbodiimide.

Depending on the nature of the starting materials used, the synthesis of the compounds according to the invention by processes A–H can be illustrated by the following equations:

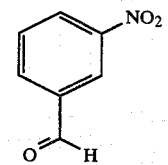

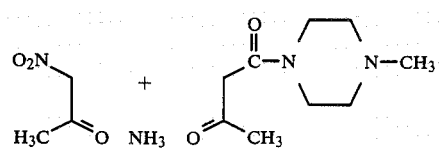

[A]

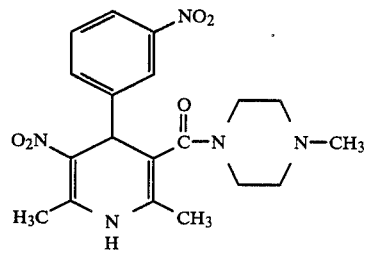

[B]

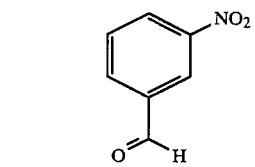

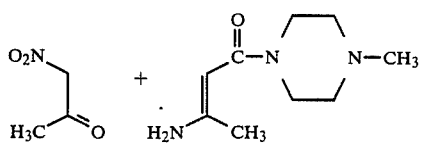

-continued
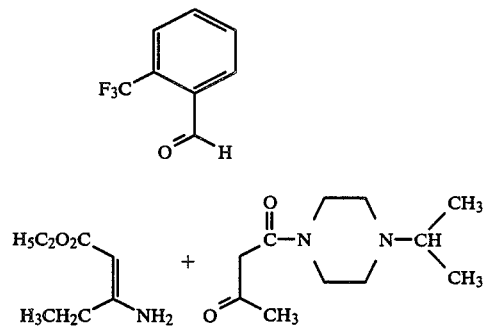
↓ [C]
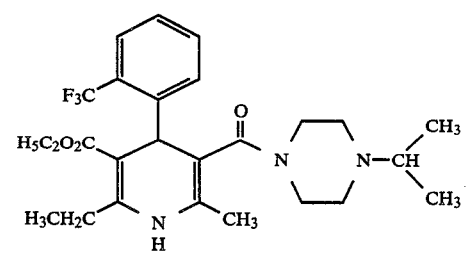
↑ [D]
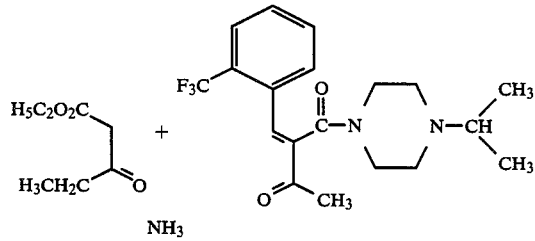
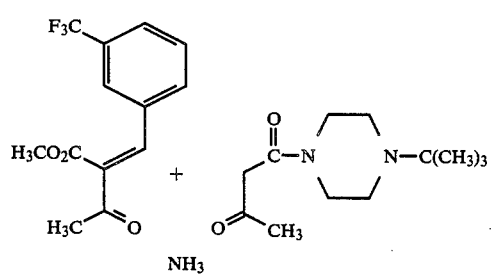
↓ [E]
-continued
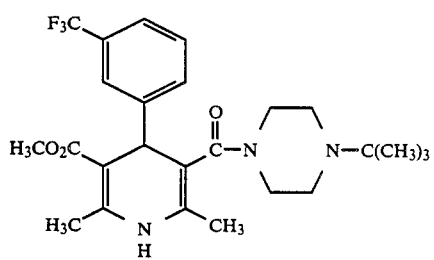
↑ [F]
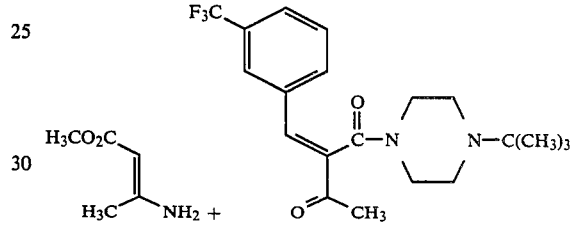
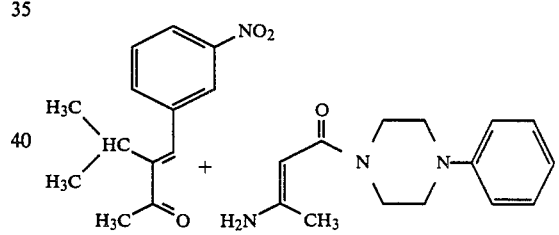
↓ [G]
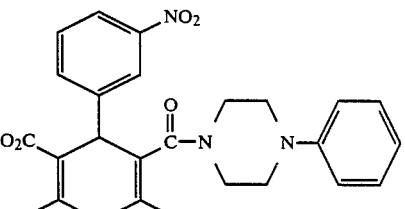
↑
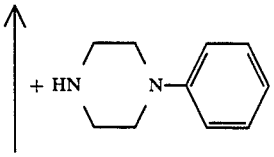

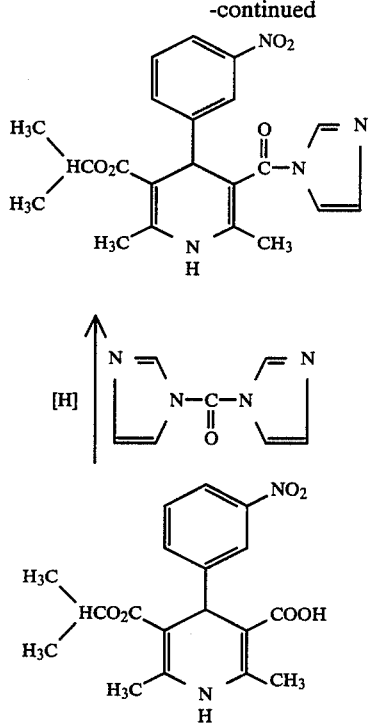

The aldehydes of the formula (II) used as starting materials are known or can be prepared by known methods [compare E. Mosettig, *Organic Reactions* Vol. III, 218 et seq. (1954); CA 59, 13929 (1963)].

The keto compounds of the formula (III) used as starting materials are known or can be prepared by known methods [compare D. Borrmann, Houben-Weyls "Methoden der organischen Chemie" ("Methods of Organic chemistry") VII/4, 230 et seq. (1968); Y. Oikawa, K. Sugano, O. Yonemitsu, *J. Org. Chem.* 43, 2087 (1978); N. Levy, C. W. Scaife, *J. Chem. Soc.* (London) 1946, 1100; C. D. Hurd, M. E. Nilson, *J. Org. Chem.* 20, 927 (1955), S. Gelin, P. Pollet, *Synth. Commun.* 1980, 805, *Tetrahedron* 34 1453 (1978)].

The enamines (VI) used as starting materials are known or can be prepared by methods known from the Literature [compare S. A. Glickmann, A. C. Cope, *J. Chem. Soc.* 67, 1017 (1945), H. Bohme, K.-H. Weisel, *Arch. Pharm.* 310, 30 (1977)].

The ylidene compounds (VIII) used as starting materials are known or can be prepared by methods known from the literature [compare G. Jones "The Knoevenagel Condensation", Organic Reactions XV, 204 et seq. (1967); for R$^5$=NO$_2$ compare w. Sassenberg A. Dornow, *Liebigs Ann. Chem.* 602, 14 (1957)].

The 1,4-dihydropyridinecarboxylic acids (IX) used as starting materials are known or can be prepared by known methods (compare German Pat. No. 28 47 237, German Pat. No. 31 30 041, German Pat. No. 33 19 956, Belgian Patent 89 39 984, German Pat. No. 33 31 808).

The piperazines (X) used as starting materials are also known.

The compounds (IV), (V) and (VII) are new. They can be prepared by methods known from the literature as described in the examples. Also according to, for example: D. Borrmann in Houben-Weyl, "Methoden der organischen Chemie" ("Methods of Organic Chemistry"), Vol. VII/4, 230 et seq. (1968); G. Jones in *Organic Reactions* Vol. VI. 204 et seq. (1967); S. A. Glickmann, A. C. Cope in *J. Amer. Chem. Soc.* 67, 1017 (1945).

Suitable diluents for processes A–G are water or all inert organic solvents. These preferably include alcohols such as methanol, ethanol and n- or iso-propanol, ethers such as diethyl ether, tetrahydrofuran, dioxane or glycol monomethyl or dimethyl ether, glacial acetic acid, pyridine, dimethylformamide, dimethyl sulphoxide, acetonitrile, hexamethyl phosphoric triamide or ethyl acetate. It is equally possible to use mixtures of the solvents mentioned.

The customary inert organic solvents are suitable for process H. These preferably include chlorinated hydrocarbons such as dichloromethane, trichloromethane, tetrachloromethane or 1,2-dichloroethane, or ethers such as diethyl ether, tetrahydrofuran, dioxane or 1,2-dimethoxyethane, or aromatic hydrocarbons such as benzene, toluene, or xylene, or acetonitrile, nitromethane, dimethylformamide, hexamethylphosphoric triamide, pyridine or ethyl acetate.

The reaction temperatures for all the processes can be varied within a relatively wide range. In general, processes A to G are carried out in a range from 10° C. to 200° C., preferably from 20° C. to 150° C. Process H is generally carried out in a range from −70° C. to +60° C., preferably from −50° C. to +40° C.

The reaction can be carried out under atmospheric pressure as well as under elevated pressure. In general, it is carried out under atmospheric pressure.

When carrying out the processes according to the invention, the ratio of the substances involved in the reaction is optional. However, in general, molar amounts of the reactants are used. In process H it has proved advantageous to use the amine in up to a 5-fold molar excess.

The compounds according to the invention exist in stereoisomeric forms which either are related as image and mirror image (enantiomers) or are not related as image and mirror image (diastereomers). The invention relates to both the antipodes and the racemic forms as well as mixtures of diastereomers. The racemic forms can be resolved in exactly the same way as the diastereomers into the stereoisomerically homogeneous constituents in a known manner (compare E. L. Eliel, *Stereochemistry of Carbon Compounds*, McGraw Hill, 1962).

The substances influence the calcium balance in eukariotic cells. Thus they are suitable as coronary therapeutic agents and can have cardioprotective or myocardium-stimulating actions. Furthermore, they can have favorable effects on the blood pressure and normalize blood sugar. They can have an effect on blood platelet aggregation.

The coronary and heart effects were found in the heart, undergoing isolated perfusion, of albino guinea-pigs of both sexes weighing 200 g, which was perfused with suitable dilutions of the sustances. For this purpose, the animals were killed, the thorax was opened, a metal cannula was tied into the aorta which had been exposed, and the left atrium was opened.

The heart was dissected out with the lungs from the thorax and connected via the aorta cannula to the perfusion apparatus with perfusion in progress. The lungs were severed at the roots of the lungs. The perfusion medium used was a Krebs-Henseleit solution (118 mmol/l NaCl, 4.8 mmol/l KCl, 1.2 mmol/l MgSO$_4$, 119 mmol/l MgSO$_4$, 25 mmol/l NaHCO$_3$, 0.013 mmol/l NaEDTA, pH 7.4, 10 mmol/l glucose) containing 1.2 mmol of CaCl$_2$, which had been filtered to remove particles before the perfusion. The hearts were perfused at 32° C. with a constant flow rate of 10 ml/min. The contractions of the heart were measured isovolumetrically using a latex balloon introduced into the left ventricle and were recorded on a high-speed pen recorder. The perfusion pressure was recorded as a measure of the coronary resistance.

The effects on contractility and coronary resistance of a few examples of the compounds according to the invention are summarized in Table 1.

TABLE 1

| Ex. No. | Conc. (μg/ml) | percentage change in contract. | coron. resistance |
|---|---|---|---|
| 22 | 1 | −5 | −6 |
|  | 10 | −52 | −19 |
| 25 | 1 | 0 | −10 |
|  | 10 | −9 | −18 |
| 57 | 1 | −49 | −35 |
|  | 10 | −93 | −38 |
| 54 | 1 | −61 | −66 |
|  | 10 | −77 | −74 |
| 60 | 1 | −30 | −9 |
|  | 10 | −76 | −12 |
| 17 | 1 | +28 | −40 |
|  | 10 | +48 | −40 |

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters), polyoxyethylene fatty alcohol ethers (for example lignin, sulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the above-mentioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

PREPARATION EXAMPLES

Example 1

3-Aminocrotonic acid 4-cyclohexylpiperazide

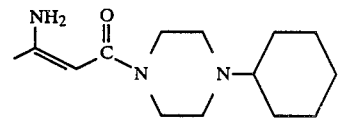

(a) 3-Oxo-butyric acid 4-cyclohexylpiperazide 24 g (0.1 mol) of 1-cyclohexylpiperazine are suspended in 150 ml of absolute tetrahydrofuran. 20 ml of triethylamine are poured in and, after 20 minutes, 18.6 g of diketene in 20 ml of tetrahydrofuran are added dropwise, and the mixture is then stirred at room temperature for 2 h. Thereafter part of the solvent is removed by distillation in vacuo, the mixture is poured onto 200 ml of ice-water, 20 g of Na$_2$CO$_3$ are added, and extraction is carried out 3 times with 50 ml of methylene chloride each time. After the organic phase has been dried with MgSO$_4$, crude 3-oxo-butyric acid 4-cyclohexylpiperazide is obtained as the residue from evaporation.

(b) 3-Aminocrotonic acid 4-cyclohexylpiperazide 0.1 mol of crude 3-oxo-butyric acid 4-cyclohexylpiperazide is dissolved in 150 ml of tetrahydrofuran and, under reflux, after addition of 0.5 g of p-toluenesulphonic acid, ammonia is passed in for 4 hours. The mixture is allowed to stand at room temperature overnight, the solvent is removed by distillation in vacuo, and the residue is crystallized from toluene/petroleum ether.

Yield: 18.6 g (74% of theory)
Melting point: 92° C.

The compounds listed in Table 2 were synthesized in analogy to Example 1.

TABLE 2

![structure: CH3-C(NH2)=CH-CO-N(piperazine)N-R4]

| Ex. No. | R⁴ | Melting point [°C.] |
|---|---|---|
| 2 | cyclopentyl | 141° C. |
| 3 | —CH₂—CH(CH₃)₂ | Oel |
| 4 | —CH₂—CH=CH₂ | Oel |
| 5 | —CH₂—C≡CH | Oel |
| 6 | CH(CH₃)₂ | 208° C. |
| 7 | cycloheptyl | 186° C. |
| 8 | phenyl | 150° C. |
| 9 | 4-CF₃-phenyl | 78° C. |
| 10 | —CH₂—CH₂—(2-CF₃-phenyl) | Oel |
| 11 | —CH₂—CO—N(morpholine)O | 75° C. |

Example 12

1,4-Dihydro-2,6-dimethyl-5-nitro-4-(2-trifluoromethylphenyl)-pyridine-3-carboxylic acid 4-cyclohexylpiperazide

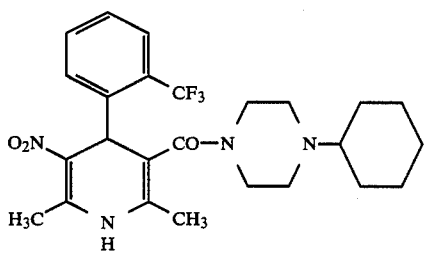

17.4 g (0.10 mol) of 2-trifluoromethylphenylbenzaldehyde, 12.0 g (0.12 mol) of nitroacetone and 25.1 g (0.10 mol) of β-aminocrotonic acid 4-cyclohexylpiperazide are heated in 50 ml of isopropanol at 60° C. for 12 hours. On cooling, the product separates out and is recrystallized from isopropanol.

Yield: 23.6 g (48% of theory)
Melting point: 240° C. (decomposition)

Example 13

5-Carboxymethyl-1,4-dihydro-2,6-dimethyl-4-(3-nitrophenyl)pyridine-3-carboxylic acid 4-cyclopentylpiperazide

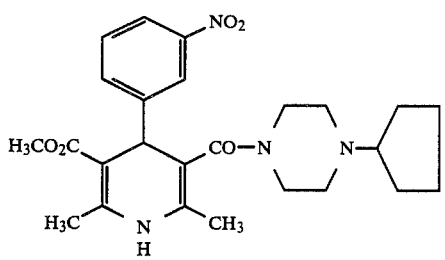

15.1 g (0.10 mol) of 3-nitrobenzaldehyde, 25.2 g (0.10 mol) of acetoacetic acid 4-cyclopentylpiperazide and 12.9 g (0.10 mol) of isopropyl β-aminocrotonate are heated to reflux in 60 ml of isopropanol for 12 hours. The product crystallizes on trituration. Recrystallization from isopropanol.

Yield: 29.4 g (61% of theory)
Melting point: 130° C.

Example 14

5-Carboxymethyl-4-(2-chlorophenyl)-dihydro-2,6-dimethylpyridine-3-carboxylic acid 4-isopropylpiperazide

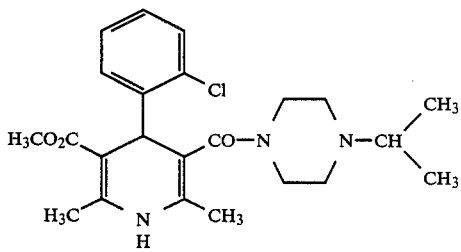

11.9 g (50 mmol) of methyl 2-chlorobenzylideneacetoacetate and 10.5 g (50 mmol) of 3-aminocrotonic acid 4-isopropylpiperazide are heated to reflux in 50 ml of isopropanol for 12 hours. The product crystallizes after cooling.

Yield: 1.7 g (79% of theory)
Melting point: 214° C.

Example 15

4-(2,1,3-Benzoxadiazol-4-yl)-1.4-dihydro-2.6-dimethyl-5-nitro-pyridine-3-carboxylic acid 4-(3-trifluoromethylphenyl) piperazide

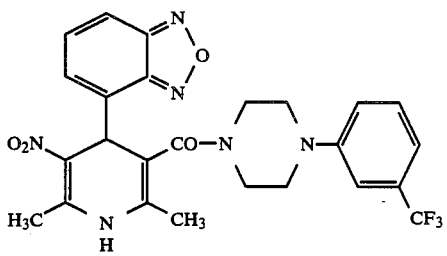

7.4 g (50 mmol) of 2.1.3-benzoxadiazole-4-aldehyde, 10 g (0.1 mol) of nitroacetone and 15.6 g (50 mmol) of 3-aminocrotonic acid 4-(3-trifluoromethylphenyl)piperazide are heated in isopropanol at 60° C. for 6 hours. The product crystallizes after part of the solvent has been evaporated off, and is recrystallized from a little isopropanol.

Yield: 8.9 g (34% of theory)
Melting point: 219° C.

Example 16

4-(2-Benzyloxyphenyl)-1,4-dihydro-2,6-dimethyl-5-nitropyridine-3-carboxylic acid 4-(2-trifluoromethylphenylethyl)piperazide

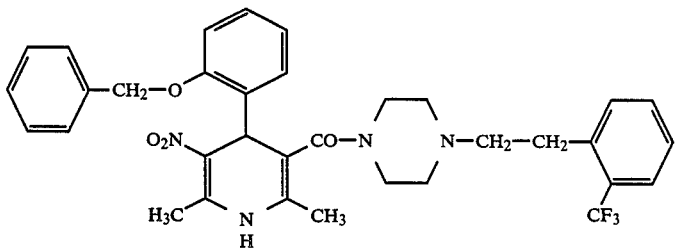

2.97 g (10 mmol) of 1-(-2-benzyloxyphenyl)-2-nitro-1-buten-3-one and 2.96 g (mmol) of 3-aminocrotonic acid 4-(2-trifluoromethylphenylethyl)piperazide are heated in 15 ml of isopropanol at 60° C. for 4 hours. After cooling, a crude product is obtained, and this is recrystallized from a littel ethanol.

Yield: 3.45 g (55% of theory)
Melting point: 198° C.

Example 17

1,4-Dihydro-2,6-dimethyl-5-nitro-4-(3-nitrophenyl)-pyridine-3-carboxylic acid 4-phenylpiperazide

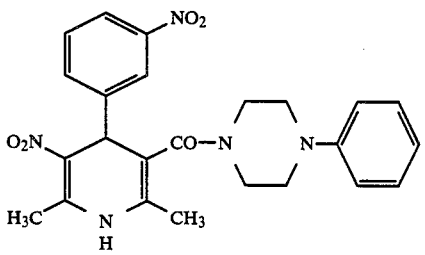

(a) 2-Acetyl-3-(3-nitrophenyl)-2-propenoic acid 4-phenylpiperazide 24.6 g (0.1 mol) of 3-oxo-butyric acid 4-phenylpiperazide in 60 ml of acetic anhydride are induced to react with 20.6 g (0.1 mol) of 1-n-butyliminomethyl-3-nitrobenzene. The mixture is then poured onto ice-water and hydrolyzed. The oil which separates out is taken up in methylene chloride, washed with dilute bicarbonate solution and water, and dried with magnesium sulphate. After the solvent has been removed by evaporation, a crude benzylidene compound is obtained and is used as such.

(b) 1,4-Dihydro-2,6-dimethyl-5-nitro-4-(3-nitrophenyl)-pyridine-3-carboxylic acid 4-phenylpiperazide 2.5 g (10 mmol) of crude 2-acetyl-3-(3-nitrophenyl)-2-propenoic acid 4-phenyl-piperazide and 2.5 g (25 mmol) of 2-amino-1-nitro-1-propene are heated in 15 ml of isopropanol at 60° C. for 6 hours. The crude product which has precipitated out is crystallized from isopropanol.

Yield: 2.7 g (58% of theory)
Melting point: 200° C.

Example 18

5-Carboxymethyl-4-(2-chlorophenyl)-1,4-dihydro-2,6-dimethylpyridine-3-carboxylic acid 4-phenyl-piperazide

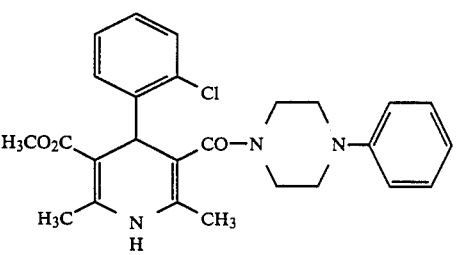

1.1 g (6.5 mmol) of carbonyldiimidazole are added to 1.60 g (5 mmol) of 5-carboxymethyl-4-(2-chlorophenyl)-1,4-dihydro-2,6-dimethyl-pyridine-3-carboxylic acid suspended in 20 ml of absolute tetrahydrofuran. The mixture is stirred at room temperature for 30 minutes and at a reflux temperature for 30 minutes. 1.62 g (10 mmol) of phenylpiperazine in 5 ml of absolute tetrahydrofuran are added to the resulting solution. This mixture is heated to reflux for 3.5 hours and then evaporated, the residue is taken up in methylene chloride, and the solution is washed successively with 1N hydrochloric acid, 1N sodium hydroxide solution and water, dried with magnesium sulphate and again evaporated. The residue crystallizes from isopropanol.

Yield: 1.82 (78% of theory)

Melting point: 182° C.

The 1.4-dihydropyridine-3-carboxylic acid piperazides which were prepared in analogy to the foregoing Examples 12 to 18 are compiled in Tables 3 and 4.

TABLE 3

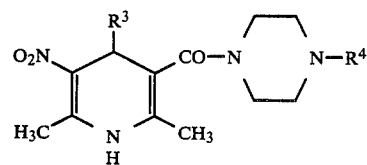

| Example No. | R³ | R⁴ | Melting point (°C.) |
|---|---|---|---|
| 19 | 3-nitrophenyl | cyclohexyl | 228 (decomp.) |
| 20 | 2-(benzyloxy)phenyl | cyclohexyl | 117 (decomp.) |
| 21 | 3-nitrophenyl | cyclopentyl | 228 (decomp.) |
| 22 | 2-(benzyloxy)phenyl | cyclopentyl | 203 (decomp.) |
| 23 | 2-(trifluoromethyl)phenyl | cyclopentyl | 261 (decomp.) |
| 24 | 2,3-dichlorophenyl | cyclopentyl | 278 (decomp.) |
| 25 | 2-(trifluoromethyl)phenyl | $CH_2-CH(CH_3)_2$ | 248 |
| 26 | 2-(benzyloxy)phenyl | $-CH_2-CH(CH_3)_2$ | 218 |
| 27 | 3-nitrophenyl | $-CH_2-CH(CH_3)_2$ | 225 (decomp.) |

TABLE 3-continued
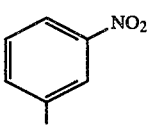
| Example No. | R³ | R⁴ | Melting point (°C.) |
|---|---|---|---|
| 28 | 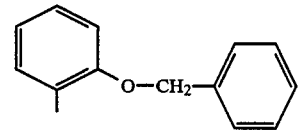 3-NO₂-phenyl | —CH₂—CH=CH₂ | 190 |
| 29 | 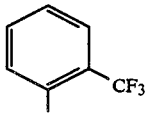 2-(benzyloxy)phenyl | —CH₂—CH=CH₂ | 223 (decomp.) |
| 30 | 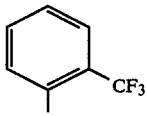 2-CF₃-phenyl | —CH₂—CH=CH₂ | 263 (decomp.) |
| 31 | 2-CF₃-phenyl | —CH₂—C≡CH | 233 (decomp.) |
| 32 | 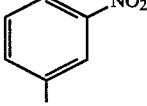 3-NO₂-phenyl | —CH₂—C≡CH | 176 |
| 33 | 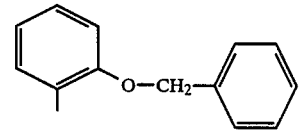 2-(benzyloxy)phenyl | —CH₂—C≡CH | 214 |
| 34 | 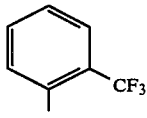 2-CF₃-phenyl | —CH₂(CH₃)₂ | 262 (decomp.) |
| 35 | 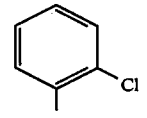 2-Cl-phenyl | —CH(CH₃)₂ | 250 (decomp.) |
| 36 | 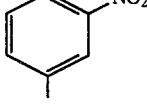 3-NO₂-phenyl | —CH(CH₃)₂ | 200 (decomp.) |
| 37 | 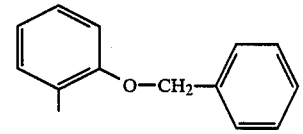 2-(benzyloxy)phenyl | —CH(CH₃)₂ | 227 |

TABLE 3-continued

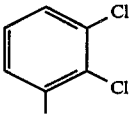

| Example No. | R³ | R⁴ | Melting point (°C.) |
|---|---|---|---|
| 38 | 2,3-dichlorophenyl | —CH(CH₃)₂ | 271 (decomp.) |
| 39 | 2,4-dichloro-6-(benzyloxy)phenyl | —CH(CH₃)₂ | resin |
| 40 | 2-(trifluoromethyl)phenyl | cycloheptyl | 274 (decomp.) |
| 41 | 3-nitrophenyl | cycloheptyl | 187 |
| 42 | 2-(benzyloxy)phenyl | cycloheptyl | 212 |
| 43 | 2-(trifluoromethyl)phenyl | phenyl | 273 |
| 44 | 2-(benzyloxy)phenyl | phenyl | 249 |
| 45 | 2-(trifluoromethyl)phenyl | 3-(trifluoromethyl)phenyl | 265 (decomp.) |
| 46 | 3-nitrophenyl | 3-(trifluoromethyl)phenyl | 121 |

TABLE 3-continued
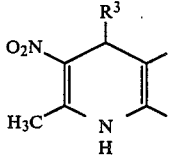
| Example No. | R³ | R⁴ | Melting point (°C.) |
|---|---|---|---|
| 47 | 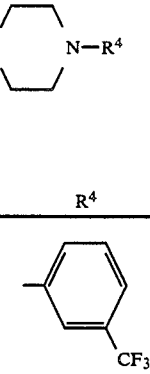 | 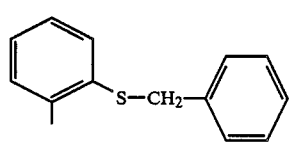 | 183 |
| 48 | 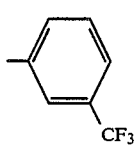 | 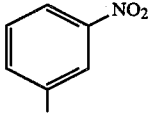 | 195 (decomp.) |
| 49 | 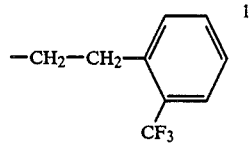 | 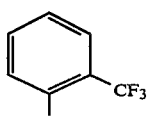 | 118 |
| 50 | 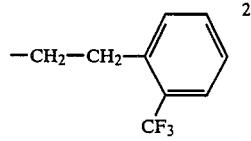 | 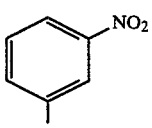 | 266 (decomp.) |
| 51 | 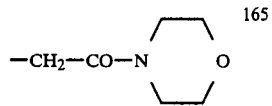 | 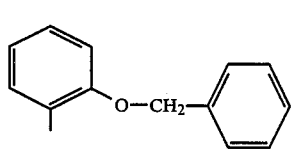 | 165 |
| 52 | 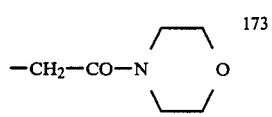 | 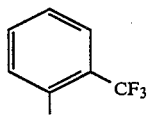 | 173 |
| 53 | 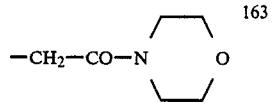 | —CH₂—CO—N⟨O⟩ | 163 |

TABLE 4

$R^5O_2C$ — [dihydropyridine core with $R^3$ at 4-position, 2,6-dimethyl, N–H, 3-carbonyl linked to piperazine N–$R^4$]

| Example No. | $R^3$ | $R^4$ | $R^5$ | Melting point (°C.) |
|---|---|---|---|---|
| 54 | 2-Cl-phenyl | cyclopentyl | $CH_3$ | 186 |
| 55 | 2,3-diCl-phenyl | cyclopentyl | $CH_3$ | 266 |
| 56 | 3-$NO_2$-phenyl | $-CH_2-C\equiv CH$ | $C_2H_5$ | 170 |
| 57 | 2-Cl-phenyl | $-CH_2-C\equiv CH$ | $CH_3$ | 202 |
| 58 | 2,3-diCl-phenyl | $-CH(CH_3)_2$ | $CH_3$ | 239 |
| 59 | 3-$NO_2$-phenyl | $-CH(CH_3)_2$ | $C_2H_5$ | 146 |
| 60 | 2-$OC_2H_5$-phenyl | $-CH(CH_3)_2$ | $C_2H_5$ | 209 (decomp.) |
| 61 | benzofurazanyl | $-CH(CH_3)_2$ | $C_2H_5$ | resin |
| 62 | 2-$OC_2H_5$-phenyl | cycloheptyl | $C_2H_5$ | 194 |
| 63 | benzofurazanyl | cycloheptyl | $C_2H_5$ | resin |

TABLE 4-continued

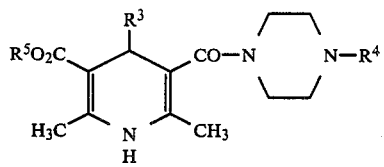

| Example No. | R³ | R⁴ | R⁵ | Melting point (°C.) |
|---|---|---|---|---|
| 64 | 3-NO₂-phenyl | phenyl | C₂H₅ | 156 |
| 65 | 3-NO₂-phenyl | 3-CF₃-phenyl | C₂H₅ | 145 |
| 66 | 2-Cl-phenyl | 3-CF₃-phenyl | CH₃ | 182 |
| 67 | 2-(3-phenyl-2-propenoyl)thiophenyl | 3-CF₃-phenyl | CH₃ | 240 (decomp.) |
| 68 | benzoxadiazolyl | 3-CF₃-phenyl | CH₃ | resin |

It is understood that the specification and examples are illustrative but not limitative of the present invention and that other embodiments within the spirit and scope of the invention will suggest themselves to those skilled in the art.

We claim:

1. A 1,4-dihydropyridine-3-carboxylic acid piperazide of formula

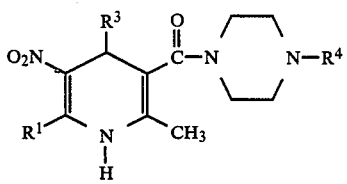

in which

R¹ represents cyano or represents straight-chain or branched $C_1$-$C_6$-alkyl which is optionally substituted by halogen, hydroxyl, benzoyloxy or acetyloxy, R³ represents $C_6$-$C_{12}$-aryl which is optionally substituted once or several times, identically or differently, by halogen, nitro, cyano, $C_1$-$C_8$-alkyl, $C_1$-$C_8$-alkoxy, $C_1$-$C_8$-alkylthio, $C_7$-$C_{14}$-aralkyl, $C_7$-$C_{14}$-aralkoxy or $C_7$-$C_{14}$-aralkylthio, it being possible for each of the aryl radicals in turn to be substituted by nitro, trifluoro-methyl, cyano, methoxy, methylthio, trifluoro-methoxy, difluoromethoxy, halogen, or $C_1$-$C_6$-alkyl, or is optionally substituted by trifluoromethyl, trifluoromethylthio, trifluoromethoxy, difluoromethoxy, amino, $C_1$-$C_6$-alkyl-amino, di-$C_1$-$C$-alkylamino, acetylamino or by benzylmethylamino, or represents a heterocycle from the group consisting of pyridyl, thienyl, furyl, pyrrolyl, quinolyl, isoquinolyl, pyrimidyl, benzoxadiazolyl, imidazolyl, thiazolyl, oxazolyl, chromenyl, or thiochromenyl, the heterocycle optionally being substituted by phenyl, $C_1$-$C_6$-alkyl, $C_1$-$C_6$-alkoxy, $C_1$-$C_6$-alkylthio, trifluoromethyl, trifluoromethoxy, trifluoromethylthio, halogen, amino, $C_1$-$C_6$-alkylamino, di-$C_1$-$C_6$-alklamino, acetylamino or benzylmethylamino, and R⁴ represents $C_6$-$C_{12}$-aryl which is optionally substituted once or several times, identically or differently, by halogen, nitro, cyano, $C_1$-$C_8$-alkyl, $C_1$-$C_8$-alkoxy, $C_1$-$C_8$-alkylthio, trifluoromethyl, trifluoromethoxy, trifluoromethylthio, difluoromethoxy, hydroxyl, amino, $C_1$–$C_6$-amino, di-$C_1$–$C_6$ alkylamino, acetylamino or benzylmethylamino, or represents straight-chain, branched or cyclic $C_1$–$C_{20}$-alkyl, $C_2$–$C_{20}$ alkenyl or $C_2$–$C_{20}$-alkynyl, each of which can optionally be substituted by halogen, $C_1$–$C_8$-alkoxy, $C_1$–$C_8$-alkyl-thio, amino, $C_1$–$C_8$-alkylamino, di-$C_1$–$C_8$-alkyl-amino, acetylamino, benzylmethylamino, piperidino, piperazino, morpholino, thiomorpholino, pyrrolidino or by $C_6$–$C_{12}$-aryl, it being possible for aryl in turn to carry one or more substituents from the group consisting of nitro, cyano, trifluoromethyl, halogen, $C_1$–$C_8$-alkyl, $C_1$–$C_8$-alkylthio or $C_1$–$C_8$-alkoxy, or is substituted by the group $COR^6$, $R^6$ representing hydrogen, representing hydroxy, representing $C_1$–$C_8$-alkoxy or representing the group

$R^7$ and $R^8$ being identical or different and denoting hydrogen, $C_1$–$C_8$-alkyl, $C_6$–$C_{12}$-aryl, $C_6$–$C_{14}$-aralkyl, acetyl or benzoyl, or $R^7$ and $R^8$ together forming a 5–7 membered saturated or unsaturated ring which can contains as further hetero atoms nitrogen, sulphur and/or oxygen, or $R^4$ represents the group $COR^6$, or a physiologically acceptable salt thereof.

2. A dihydropyridine or salt according to claim 1, in which $R^1$ represents straight-chain or branched $C_1$–$C_4$-alkyl, which is optionally substituted by one or more fluorine, chlorine, bromine, hydroxyl, benzoyloxy or acetyloxy, $R^3$ represents phenyl which is optionally substituted up to four times, identically or differently, by fluorine, chlorine, bromine, nitro, cyano, $C_1$–$C_6$-alkyl, $C_1$–$C_6$-alkoxy, $C_1$–$C_6$-alkylthio, benzyl, benzyloxy or benzylthio, it being possible for each of the phenyl radicals in turn to be substituted by nitro, trifluoromethyl, trifluoromethoxy, trifluoromethylthio, methoxy, fluorine, chlorine, bromine or $C_1$–$C_4$-alkyl, or is substituted by trifluoromethyl, trifluoromethoxy, difluoromethoxy, amino, $C_1$–$C_4$-alkylamino, di-$C_1$–$C_4$-alkylamino or acetylamino, or represents pyridyl, thienyl, furyl, pyrimidyl, benzoxadiazolyl, 2-phenyl-thiochromen-8-yl or quinolyl, and $R^4$ represents phenyl which is optionally substituted up to four times, identically or differently, by fluorine, chlorine, bromine, nitro, cyano, $C_1$–$C_6$-alkyl, $C_1$–$C_6$-alkoxy, $C_1$–$C_6$-alkylthio, trifluoromethyl, trifluoromethoxy, difluoromethoxy, hydroxyl, amino, $C_1$–$C_3$-alkylamino, di-$C_1$–$C_3$-alkylamino or acetylamino, or represents straight-chain, branched or cyclic $C_1$–$C_{15}$-alkyl, $C_2$–$C_{15}$-alkenyl or $C_2$–$C_{15}$-alkynyl, each of which is optionally substituted by fluorine, chlorine, bromine, $C_1$–$C_6$-alkoxy, $C_1$–$C_6$-alkylthio, amino, $C_1$–$C_6$-alkylamino, di-$C_1$–$C_6$-alkylamino, acetylamino, benzoylamino or by phenyl, it being possible for the phenyl radical in turn to carry one to three substituents from the group consisting of nitro, trifluoromethyl, fluorine, chlorine, bromine, $C_1$–$C_6$-alkyl, $C_1$–$C_6$-alkoxy or $C_1$–$C_6$-alkylthio, or is substituted by the group $COR^6$, $R^6$ represents hydrogen, representing hydroxyl, representing $C_1$–$C_6$-alkoxy or representing the group

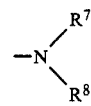

$R^7$ and $R^8$ being indentical or different and representing hydrogen, representing $C_1$–$C_6$-alkyl, representing phenyl, representing benzyl, representing acetyl or representing benzoyl, or $R^7$ and $R^8$ together with the nitrogen atom forming a heterocycle from the group consisting of pyrrolidine, piperidine, morpholine, thiomorpholine, imidazolidine, piperazine or pyrroline, or $R^4$ represents the group of the formula $COR^6$.

3. A dihydropyridine or salt according to claim 1, in which $R^1$ represents methyl or ethyl, each of which is optionally substituted by chlorine, bromine or acetyloxy, $R^3$ represents phenyl which is optionally substituted up to three times, identically or differently, by fluorine, chlorine, nitro, cyano, $C_1$–$C_4$-alkyl, $C_1$–$C_4$-alkoxy, $C_1$–$C_4$-alkylthio, benzyl, benzyloxy or benzylthio, it being possible for the phenyl radicals in turn to be substituted up to twice by nitro, trifluoromethyl, methoxy, fluorine, chlorine, methyl or ethyl, or is substituted by trifluoromethyl or trifluoromethoxy, or represents pyridyl, thienyl, furyl, pyrimidyl or benzoxadiazolyl or 2-phenyl-thiochromen-9-yl, and $R^4$ represents phenyl which is optionally substituted up to twice, identically or differently, by fluorine, chlorine, nitro, $C_1$–$C_4$-alkyl, $C_1$–$C_4$-alkoxy, $C_1$–$C_4$-alkylthio or trifluoromethoxy, or represents straight-chain, branched or cyclic $C_1$–$C_{10}$-alkyl, $C_2$–$C_{10}$-alkenyl or $C_2$–$C_{10}$-alkynyl, each of which is optionally substituted by fluorine, chlorine, $C_1$–$C_4$-alkoxy, $C_1$–$C_4$-alkylthio, amino, $C_1$–$C_4$-alkylamino, di-$C_1$–$C_4$-alkylamino, acetylamino or by phenyl, it being possible for phenyl in turn to carry one to two substituents from the group consisting of nitro, trifluoromethyl, fluorine, chlorine, $C_1$–$C_4$-alkoxy or $C_1$–$C_4$-alkyl, or is substituted by the group $COR^6$, $R^6$ represents hydrogen, representing hydroxyl, representing $C_1$–$C_4$-alkoxy or representing the group

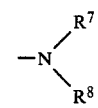

$R^7$ and $R^8$ being identical or different and representing hydrogen, representing $C_1$–$C_4$ alkyl, representing phenyl, representing benzyl or representing acetyl, or $R^7$ and $R^8$, together with the nitrogen atom, form a heterocycle from the group consisting of pyrrolidine, piperidine, morpholine or thiomorpholine, or $R^4$ represents the group $COR^6$.

4. A dihydropyridine according to claim 1, wherein such compound is 1,4-dihydro-2,6-dimethyl-5-nitro-4-(2-trifluoromethyl-phenyl)-pyridine-3-carboxylic acid 4-cyclohexylpiperazide of the formula

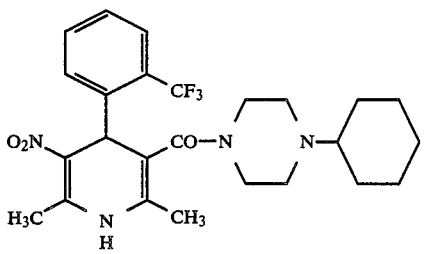

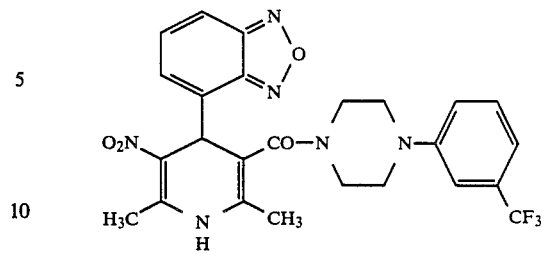

or a physiologically acceptable salt thereof.

5. A dihydropyridine according to claim 1, wherein such compound is 4-(2,1,3-benzoxadiazol-4-yl)-1,4-dihydro-2,6-dimethyl-5-nitro-pyridine-3-carboxylic acid 4-(3-trifluoromethyl-phenyl) piperazide of the formula or a physiologically acceptable salt thereof.

6. A dihydropyridine according to claim 1, wherein such compound is 4-(2-benzyloxyphenyl)-1,4-dihydro-2,6-dimethyl-5-nitro-pyridine-3-carboxylic acid 4-(2-trifluoromethylphenyl-ethyl)piperazide of the formula

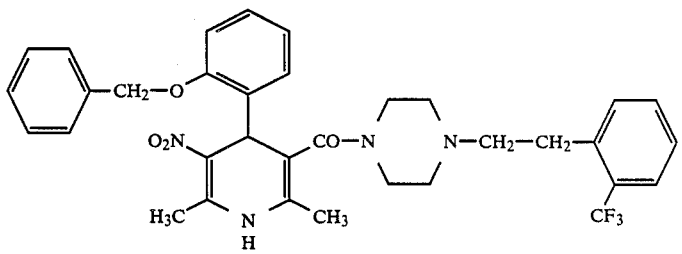

or a physiologically acceptable salt thereof.

7. A cardioprotective and myocardium-stimulating composition comprising an amount effective therefor of a compound or salt according to claim 1 in admixture with a diluent.

8. A unit dose of a composition according to claim 7 in the form of a tablet, capsule or ampule.

9. A method of normalizing circulation in a patient in need thereof which comprises administering to such patient an amount effective therefor of a compound or salt according to claim 1.

10. The method according to claim 9, wherein such compound is
1,4-dihydro-2,6-dimethyl-5-nitro-4-(2-trifluoromethylphenyl)-pyridine-3-carboxylic acid 4-cyclohexylpiperazide,
4-(2,1,3-benzoxadiazol-4-yl)-1,4-dihydro-2,6-dimethyl-5-nitro-pyridine-3-carboxylic acid 4-(3-trifluoromethyl-phenyl)piperazide, or 4-(2-benzyloxyphenyl-1,4-dihydro-2,6-dimethyl-5-nitropyridine-3-carboxylic acid 4-(2-trifluoro-methylphenylethyl)piperazide,
or a physiologically acceptable salt thereof.

* * * * *

UNITED STATES PATENT AND TRADEMARK OFFICE
CERTIFICATE OF CORRECTION

PATENT NO. : 4,753,936

DATED : June 28, 1988

INVENTOR(S) : Gerhard Franckowiak, et al

It is certified that error appears in the above-identified patent and that said Letters Patent is hereby corrected as shown below:

| | |
|---|---|
| Col. 2, line 58 | Delete "or acetylamino" second instance |
| Col. 2, line 64 | After "trifluoromethyl" insert --trifluoromethoxy-- |
| Col. 5, line 42 | Delete "$R_3$" and substitute --$R^3$-- |
| Col. 9, line 46 | Delete "Literature" and substitute --literature-- |
| Col. 10, line 58 | Delete "sustances" and substitute --substances-- |
| Col. 15, line 50 | Delete "littel" and substitute --little-- |
| Col. 29, line 1 | Delete "$C_1$-$C_6$-amino" and substitute --$C_1$-$C_6$-alkylamino-- |

Signed and Sealed this

Tenth Day of January, 1989

Attest:

DONALD J. QUIGG

*Attesting Officer*  *Commissioner of Patents and Trademarks*